Figure 1:
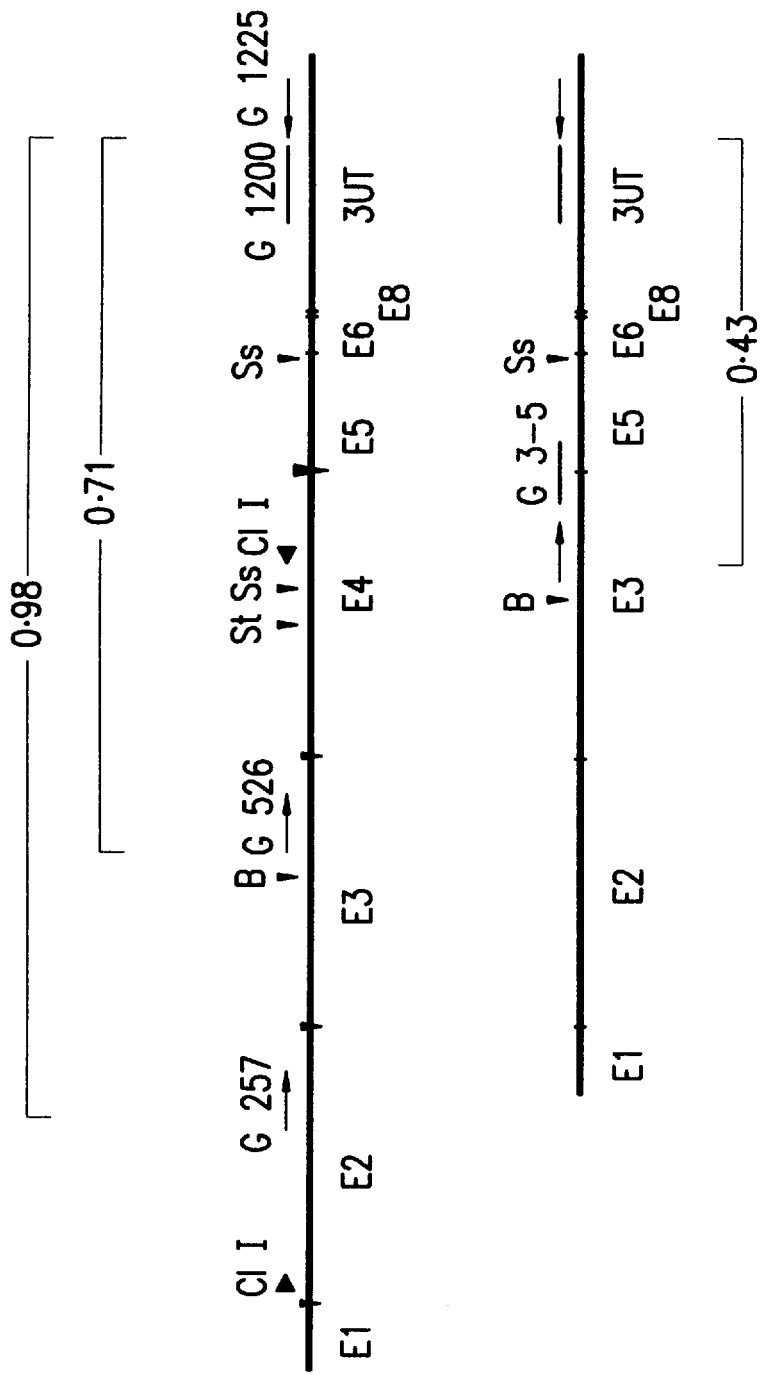

United States Patent [19]

Carosella et al.

[11] Patent Number: 5,856,442
[45] Date of Patent: Jan. 5, 1999

[54] TRANSCRIPTS OF THE MHC CLASS I HLA-G GENE AND THEIR APPLICATIONS

[75] Inventors: Edgardo Delfino Carosella, Paris; Philippe Moreau, Viry-Chatillon; Eliane Gluckman, Paris; Marek Kirszenbaum, Orsay, all of France

[73] Assignee: Commissariat a l'Energie Atomique, Paris, France

[21] Appl. No.: 406,057

[22] Filed: Mar. 17, 1995

[30] Foreign Application Priority Data

Mar. 18, 1994 [FR] France .................................. 94 03179

[51] Int. Cl.$^6$ .................... C07K 13/00; C07K 16/00; A61K 39/395; G01N 33/53
[52] U.S. Cl. ............. 530/350; 530/388.73; 530/388.75; 530/389.6; 530/403; 530/387.1; 530/387.3; 530/387.9; 530/389.1; 424/156.1; 424/184.1; 424/278.1; 435/343; 435/343.1; 435/7.1; 435/7.2; 435/7.9; 435/6; 436/538
[58] Field of Search .................... 435/7.1–7.7, 6, 435/343, 343.1; 530/300, 350, 388.1, 388.73, 388.75, 389.6, 403, 387.1–387.3, 387.9, 388.7, 389.1; 424/85.8, 156.1, 184.1, 278.1; 514/2; 436/538

[56] References Cited

PUBLICATIONS

Shukla, et al., Nucleic Acids Research, vol. 18, No. 8, (1990), p. 2189.

Ishitani, et al., Proceedings of the National Academy of Sciences of the USA, vol. 89, No. 9, (1992), pp. 3947–3951.

Geraghty, et al., Proceedings of the National Academy of Sciences of the USA, vol. 84, No. 24, (1987), pp. 9145–9149.

Geraghty, Current Opinion in Immunology, vol. 5, No. 1 (1993), pp. 3–7.

Geraghty, et al., The FASEB Journal, vol. 7, No. 4 (1990), p. A2216.

Talmadge et al. Advanced Drug Delivery Reviews 10: 247–299, 1993.

Ellis et al. J. of Immunology 144: 731–735, 1990.

*Primary Examiner*—W. Gary Jones
*Assistant Examiner*—Dianne Rees
*Attorney, Agent, or Firm*—Oblon, Spivak, McClelland, Maier & Neustadt, P.C.

[57] ABSTRACT

Transcripts of the major histocompatibility complex (MHC) Class I HLA-G gene which are present in foetal trophoblasts and/or in adult circulating mono-nuclear cells, as well as methods of using these. Either the said transcripts comprise, in succession in the 5' to 3' direction: a fragment encoding the signal peptide (exon 1), a fragment encoding the α1 domain (exon 2), a fragment encoding the α2 domain (exon 3), a fragment encoding the transmembrane TM domain (exon 5), a fragment encoding the cytoplasmic domain (exon 6) and the 3' untranslated fragment (exon 8), which sequence is designated HLA-G4, or the said transcripts comprise intron 4.

21 Claims, 14 Drawing Sheets

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 440 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:1:

```
CCAATGTGGC  TGAACAAAGG  AGAGCCTACC  TGGAGGGCAC  GTGCGTGGAG  TGGCTCCACA    60
GATACCTGGA  GAACGGGAAG  GAGATGCTGC  AGCGCGCGGA  GCAGTCTTCC  CTGCCCACCA   120
TCCCCATCAT  GGGTATCGTT  GCTGGCCTGG  TTGTCCTTGC  AGCTGTAGTC  ACTGGAGCTG   180
CGGTCGCTGC  TGTGCTGTGG  AGAAGAAGAG  CTCAGATTGA  AAAGGAGGGA  GCTACTCTCA   240
GGCTGCAATG  TGAAACAGCT  GCCCTGTGTG  GGACTGAGTG  GCAAGTCCCT  TTGTGACTTC   300
AAGAACCCTG  ACTTCTCTTT  TGCAGAGACC  AGCCCACCCC  TGTGCCCACC  ATGACCCTCT   360
TCTCATGCTG  AACTGCATTC  CTTCCCCAAT  CACCTTTCCT  GTTCCAGAAA  AGGGGCTGGG   420
ATGTCTCCGT  CTCTGTCTCA                                                   440
```

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:2:

```
GGAAGAGGAG  ACACCGGAAC  A                                                 21
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:3:

```
CCAATGTGGC  TGAACAAAGG                                                    20
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:4:

```
CCCCTTTTCT  GGAACAGGAA                                                    20
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:5:

TGAGACAGAG ACGGAGACAT                                                                  20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:6:

CAGCGCGCGG AGCAGTCTTC                                                                  20

( 2 ) INFORMATION FOR SEQ ID NO:7:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Asn  Val  Ala  Glu  Gln  Arg  Arg  Ala  Tyr  Leu  Glu  Gly  Thr  Cys  Val  Glu
 1                   5                        10                       15

Trp  Leu  His  Arg  Tyr  Leu  Glu  Asn  Gly  Lys  Glu  Met  Leu  Gln  Arg  Ala
               20                        25                       30

Glu  Gln  Ser  Ser  Leu  Pro  Thr  Ile  Pro  Ile  Met  Gly  Ile  Val  Ala  Gly
          35                        40                       45

Leu  Val  Val  Leu  Ala  Ala  Val  Val  Thr  Glu  Ala  Ala  Val  Ala  Ala  Val
     50                        55                       60

Leu  Trp  Arg  Lys  Lys  Ser  Ser  Asp
 65                       70
```

( 2 ) INFORMATION FOR SEQ ID NO:8:

( i ) SEQUENCE CHARACTERISTICS:
        ( A ) LENGTH: 145 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Asn  Val  Ala  Glu  Gln  Arg  Arg  Ala  Tyr  Leu  Glu  Gly  Thr  Cys  Val  Glu
 1                   5                        10                       15

Trp  Leu  His  Arg  Tyr  Leu  Glu  Asn  Gly  Lys  Glu  Met  Leu  Gln  Arg  Ala
               20                        25                       30

Asp  Pro  Pro  Lys  Thr  His  Val  Thr  His  His  Pro  Val  Phe  Asp  Tyr  Glu
          35                        40                       45
```

|     | Ala | Thr | Leu | Arg | Cys | Trp | Ala | Leu | Gly | Phe | Tyr | Pro | Ala | Glu | Ile | Ile |
|     |     | 50  |     |     |     |     | 55  |     |     |     |     | 60  |     |     |     |     |

|     | Leu | Thr | Trp | Gln | Arg | Asp | Gly | Glu | Asp | Gln | Thr | Gln | Asp | Val | Glu | Leu |
|     | 65  |     |     |     |     | 70  |     |     |     |     | 75  |     |     |     |     | 80  |

|     | Val | Glu | Thr | Arg | Pro | Ala | Gly | Asp | Gly | Thr | Phe | Gln | Lys | Trp | Ala | Ala |
|     |     |     |     |     | 85  |     |     |     |     | 90  |     |     |     |     |     | 95  |

|     | Val | Val | Val | Pro | Ser | Gly | Glu | Glu | Gln | Arg | Tyr | Thr | Cys | His | Val | Gln |
|     |     |     |     | 100 |     |     |     |     | 105 |     |     |     |     | 110 |     |     |

|     | His | Glu | Gly | Leu | Pro | Glu | Pro | Leu | Met | Leu | Arg | Trp | Ser | Lys | Glu | Gly |
|     |     |     | 115 |     |     |     |     |     | 120 |     |     |     |     | 125 |     |     |

|     | Asp | Gly | Gly | Ile | Met | Ser | Val | Arg | Glu | Ser | Arg | Ser | Leu | Ser | Glu | Asp |
|     |     |     | 130 |     |     |     |     | 135 |     |     |     |     | 140 |     |     |     |

Leu
145

( 2 ) INFORMATION FOR SEQ ID NO:9:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

|     | Gln | Ser | Glu | Ala | Asn | Pro | Pro | Lys | Thr | His | Val | Thr | His | His | Pro | Val |
|     | 1   |     |     |     | 5   |     |     |     |     | 10  |     |     |     |     | 15  |     |

|     | Phe | Asp | Tyr | Glu | Ala | Thr | Leu | Arg | Cys | Trp | Ala | Leu | Gly | Phe | Tyr | Pro |
|     |     |     |     | 20  |     |     |     |     | 25  |     |     |     |     | 30  |     |     |

|     | Ala | Glu | Ile | Ile | Leu | Thr | Trp | Gln | Arg | Asp | Gly | Glu | Asp | Gln | Thr | Gln |
|     |     |     |     | 35  |     |     |     |     | 40  |     |     |     |     | 45  |     |     |

|     | Asp | Val | Glu | Leu | Val | Glu | Thr | Arg | Pro | Ala | Gly | Asp | Gly | Thr | Phe | Gln |
|     |     | 50  |     |     |     |     | 55  |     |     |     |     | 60  |     |     |     |     |

|     | Lys | Trp | Ala | Ala | Val | Val | Val | Pro | Ser | Gly | Glu | Glu | Gln | Arg | Tyr | Thr |
|     | 65  |     |     |     |     | 70  |     |     |     |     | 75  |     |     |     |     | 80  |

|     | Cys | His | Val | Gln | His | Glu | Gly | Leu | Pro | Glu | Pro | Leu | Met | Leu | Arg | Trp |
|     |     |     |     |     | 85  |     |     |     |     | 90  |     |     |     |     | 95  |     |

|     | Ser | Lys | Glu | Gly | Asp | Gly | Gly | Ile | Met | Ser | Val | Arg | Glu | Ser | Arg | Ser |
|     |     |     |     | 100 |     |     |     |     | 105 |     |     |     |     | 110 |     |     |

|     | Leu | Ser | Glu | Asp | Leu |
|     |     |     |     | 115 |     |

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:10:

GAGGCATCAT GTCTGTTAGG                                                                             20

( 2 ) INFORMATION FOR SEQ ID NO:11:

( i ) SEQUENCE CHARACTERISTICS:
        ( A ) LENGTH: 20 base pairs
        ( B ) TYPE: nucleic acid (C) STRANDEDNESS: single
        (D) TOPOLOGY: linear (ii) MOLECULE TYPE: cDNA to mRNA (xi) SEQUENCE DESCRIPTION: SEQ ID NO:11:

AAAGGAGGTG AAGGTGAGGG 20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:12:

ACCAGAGCGA GGCCAACCCC 20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:13:

CCACCACCCT GTCTTTGACT 20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:14:

ATCATGGGTA TCGTTGCTGG 20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:15:

CTAATGTGTC TCTCACGGCT 20

TRANSCRIPTS OF THE MHC CLASS I HLA-G GENE AND THEIR APPLICATIONS

The present invention relates to transcripts of the major histocompatibility complex (MHC) class I HLA-G gene which are present in foetal trophoblasts and/or in adult circulating mononuclear cells, and to their applications.

The antigens of the major histocompatibility complex (MHC) divide into several classes, i.e. class I antigens (HLA-A, HLA-B and HLA-C) which exhibit 3 globular domains ($\alpha 1$, $\alpha 2$ and $\alpha 3$), of which the $\alpha 3$ domain is associated with $\beta 2$ microglobulin, class II antigens (HLA-DP, HLA-DQ and HLA-DR) and class III antigens (complement).

In addition to the aforementioned antigens, the class I antigens include other antigens, termed non-classical class I antigens, in particular the antigens HLA-E, HLA-F and HLA-G; this latter, in particular, is expressed by the extravillous trophoblasts of the normal human placenta.

The sequence of the HLA-G gene (HLA-6.0 gene) has been described by GERAGHTY et al., (Proc. Natl. Acad. Sci. USA, 1987, 84, 9145–9149): it comprises 4,396 base pairs and exhibits an intron/exon organization which is homologous to that of the HLA-A, HLA-B and HLA-C genes. More precisely, this gene comprises 8 exons and an untranslated, 3'UT, end, with the following respective correspondence: exon 1: signal sequence, exon 2: $\alpha 1$ domain, exon 3: $\alpha 2$ domain, exon 4: $\alpha 3$ domain, exon 5: transmembrane region, exon 6: cytoplasmic domain I, exon 7: cytoplasmic domain II, exon 8: cytoplasmic domain III and 3' untranslated region (GERAGHTY et al., mentioned above, ELLIS et al., J. Immunol., 1990, 144, 731–735). However, the HLA-G gene differs from the other class I genes in that the in-frame translation termination codon is located at the second codon of exon 6; as a result, the cytoplasmic region of the protein encoded by this gene HLA-6.0 is considerably shorter than that of the cytoplasmic regions of the HLA-A, HLA-B and HLA-C proteins.

Contrary to the other class I antigens, this HLA-G antigen (G 6.0 and BeWO.G7 clones) is apparently not polymorphic and is not expressed in cell types other than trophoblasts (ELLIS et al., J. Immunol., 1990, mentioned above).

Other HLA-G clones have been isolated (TAMAKI et al., Microbiol. Immunol., 1993, 37, 8, 633–640); in particular, the HLA-G clone designated 7.0E was isolated from a Japanese placenta and its amino acid sequence was found to be identical to that of the abovementioned G6.0 and BeWO.G7 clones. Furthermore, the authors of Tamaki et al. demonstrate that a certain heterogeneity can exist within the HLA-G genes.

These HLA-G antigens are mainly expressed by the cytotrophoblast cells of the placenta; however, HLA-G mRNA has been encountered in the tissues of the eye and in foetal liver (ISHITANI et al., Proc. Natl. Acad. Sci. USA, 1992, 89, 3947–3951; with the numbering corresponding to that of the HLA 6.0 sequence as described in SHUKLA et al., Nucleic Acid Research, 1990, 18, 8, 2189).

The HLA-G antigens expressed by the cytotrophoblasts are regarded as playing a role in the protection of the placenta (absence of rejection). Furthermore, in so far as the HLA-G antigen is monomorphic, it can also be implicated in the growth or the function of the placental cells (KOVATS et al., Science, 1990, 248, 220–223).

Other research studies relating to this non-classical class I antigen (ISHITANI et al., Proc. Natl. Acad. Sci. USA, 1992, 89, 3947–3951) have demonstrated that the primary transcript of the HLA-G gene can be spliced in various ways and produces at least 3 distinct mature 3 mRNAs; the primary HLA-G transcript supplies a complete copy (G1) of 1,200 bp, a fragment of 900 bp (G2) and a fragment of 600 bp (G3).

The G1 transcript does not include exon 7 and corresponds to the sequence described by ELLIS et al. (mentioned above), that is, it encodes a protein which comprises a leader sequence, three external domains, a transmembrane region and a cytoplasmic sequence. The G2 mRNA does not include exon 3, that is, it encodes a protein in which the $\alpha 1$ and $\alpha 3$ domains are directly connected; the G3 mRNA contains neither exon 3 nor exon 4, that is it encodes a protein in which the $\alpha 1$ domain and the transmembrane sequence are directly connected.

The splicing which results in the reproduction of HLA-G2 antigen leads to an adenine (A) (originating from the domain encoding $\alpha 1$) being joined to an AC sequence (from the domain encoding $\alpha 3$), resulting in the creation of an AAC (asparagine) codon in place of the GAC (aspartic acid) codon which is encountered at the beginning of the sequence encoding the $\alpha 3$ domain in HLA-G1.

The splicing which is generated in order to obtain HLA-G3 does not result in a novel codon being formed in the splicing zone.

The authors of this article have also analysed the different proteins which are expressed: the 3 mRNAs are translated into protein in the cell line .221-G.

The authors of this article conclude that HLA-G plays a fundamental role in protecting the placenta from a maternal immune response (induction of immune tolerance). However, it is made clear that the role of the G3 protein, which does not contain the $\alpha 3$ domain, has not been established.

The complexity of the MHC and the role of the HLA-G antigen in tolerance mechanisms have led the inventors to search at least for an HLA-G transcript which could, at one and the same time:

readily be demonstrated in peripheral blood, be suitable for expressing, under appropriate conditions, a protein, preferably soluble, which is suitable as a tolerance agent, enable immature stem cells to be selected which are suitable for being employed in bone marrow transplants, and also enable foetal cells in which this gene is being expressed to be demonstrated in the maternal blood.

Consequently, the underlying object of the present invention is to provide sequences derived from an mRNA of the HLA-G gene which is suitable for solving all the problems set out above.

Such sequences can be applied, in particular:

in the separation, from a sample of maternal blood, of foetal cells, in a procedure for enriching with immature stem cells which are suitable for being employed in marrow transplants, and in the specific separation of circulating mononuclear cells, and in the preparation of a immunomodulating drug.

The present invention relates to a cDNA sequence derived from an mRNA of the human MHC HLA-G gene, which sequence is characterized in that it comprises, in succession in the 5' to 3' direction:

a fragment encoding the signal peptide (exon 1), a fragment encoding the $\alpha 1$ domain (exon 2), a fragment encoding the α2 domain (exon 3), a fragment encoding the transmembrane TM domain (exon 5), a fragment encoding the cytoplasmic domain (exon 6), and the untranslated 3' fragment (exon 8), with this sequence being designated HLA-G 3-5 or according to the now in force nomenclature HLA-G4.

The distinctive feature of a sequence of this nature is that it does not include exon 4 and demonstrates all of the properties enumerated above and is, in particulier, able to be detected in adult circulating mononuclear cells.

Mononuclear cells mean all mononuclear cells of the peripheral blood, except natural killer cells (NK cells and other large granular lymphocytes (LGL)).

According to an advantageous embodiment of the invention, the said sequence comprises, in succession in the 5' to 3' direction:

the fragment encoding the α2 domain (exon 3), the fragment encoding the transmembrane TM domain (exon 5), the fragment encoding the cytoplasmic domain (exon 6), and the untranslated 3' fragment (exon 8).

In conformity with the invention, such a sequence which encodes a protein in which the α2 domain and the HLA-G transmembrane sequence are directly connected exhibits the following SEQ ID NO:1:

The present invention also relates to oligonucleotide fragments of the sequence, without exon 4, according to the invention; of these fragments, the numbering of which corresponds to that of the HLA 6.0 sequence, as described in SHUKLA et al., mentioned above, the following may be cited:

GGA AGA GGA GAC ACCG GAA CA (SEQ ID NO: 2), designated G.257 (+), located in exon 2 and corresponding to the 257-276 fragment of the said cDNA sequence;

CCA ATG TGG CTG AAC AAA GG (SEQ ID NO: 3) designated G.526 (+), located in exon 3 and corresponding to the 526-545 fragment of the said cDNA sequence;

CCC CTT TTC TGG AAC AGG AA (SEQ ID NO: 4), designated G.1200 (−) and corresponding to the 1200-1219 fragment of the said cDNA sequence;

TGA GAC AGA GAC GGA GAC AT (SEQ ID NO: 5), designated G.1225 (−) and corresponding to the 1225-1244 fragment of the said cDNA sequence;

CAG CGC GCG GAG CAG TCT TC (SEQ ID NO: 6), designated G.3.5 (+) and corresponding to the exon 3-exon 5 junction of the said cDNA sequence.

The present invention also relates to nucleotide probes which are characterized in that they consist of a nucleotide sequence as defined above, or of a fragment thereof, which is labelled using a label such as a radioactive isotope, an appropriate enzyme or a fluorochrome.

According to an advantageous embodiment of the said probe, it displays the specific sequence, of SEQ ID NO:6 above, of the transcript without exon 4, according to the invention.

CC AAT GTG GCT GAA CAA AGG AGA GCC TAC CTG GAG GGC AGC

TGC GTG GAG TGG CTC CAC AGA TAC CTG GAG AAC GGG AAG GAG

ATG CTG CAG CGC GCG G$_3$/$^5$ AG CAG TCT TCC CTG CCC ACC ATC

CCC ATC ATG GGT ATC GTT GCT GGC CTG GTT GTC CTT GCA GCT

GTA GTC ACT GGA GCT GCG GTC GCT GCT GTG CTGT TGG TGG AGX$_1$ AAG

AAG AGC TCA G$_5$/$^6$ AT TGA AAA GGA GGG AGC TAC TCT CAG GCT

GCA A$_6$/$^8$ TG TGA$^8$/ AACAGCTGCCCTGTGTGGGACTGAGTGGCAAGTCCCTTT

GTGACTTCAAGAACCCTGACTTCTCTTX$_2$ TGCAGAGACCAGCCCACCCCTGTGCCC

ACCATGACCCTCTTX$_3$ CTCATGCTGAACTGCATTV=CCTTCCCCAATCACCTTTCCTGT

TCCAGAAAAGGGGCTGGGARGTCTCCGTCTCTGTCTCA in which

X$_1$ represents G or A,

X$_2$ represents C or G, and

X$_3$ represents T or C, and comprises 0.43 kb.

Unexpectedly, a transcript of this nature is detected in trophoblasts (first trimester of gestation) as well as in adult circulating mononuclear cells.

The present invention also relates to a transcription product of the human MHC HLA-G gene, which product is characterized in that it includes, proceeding from the 5' end:

a fragment encoding the peptide signal (exon 1), a fragment encoding the α1 domain (exon 2), a fragment encoding the α2 domain (exon 3), a fragment encoding the transmembrane TM domain (exon 5), and a fragment encoding the HLA-G cytoplasmic domain (exon 6), and in that it comprises 0.43 kb.

According to another advantageous embodiment of the said probe, it displays the sequence of SEQ ID NO:4 above; a probe of this nature is suitable for detecting all the transcription products of the human MHC HLA-G gene.

The present invention also relates to primers which are suitable for being employed to amplify a nucleotide sequence according to the invention, such as defined above (without exon 4).

According to an advantageous embodiment of the said primers, a preferred pair of primers comprises:

(1) GGA AGA GGA GAC ACCG GAA (SEQ ID NO:2)

(2) TGA GAC AGA GAC GGA GAC AT (SEQ ID NO:5).

According to another advantageous embodiment of the said primers, another preferred pair of primers comprises:

(3) CCA ATG TGG CTG AAC AAA GG (SEQ ID NO:3)

(4) TGA GAC AGA GAC GGA GAC AT (SEQ ID NO:4).

Unexpectedly, the Inventors have found that other transcripts may be detected in adult circulating mononuclear cells.

Among these transcripts, the following may be cited:

a) the transcript designated HLA-G5, comprising in succession in the 5' to 3' direction:
   a fragment encoding the signal peptide (exon 1),
   a fragment encoding the α1 domain (exon 2),
   a fragment encoding the α2 domain (exon 3),
   a fragment encoding the α3 domain (exon 4),
   intron 4,
   a fragment encoding the transmembrane TM domain (exon 5),
   a fragment encoding the cytoplasmic domain (exon 6) and the untranslated 3' fragment (exon 8).

The presence of intron 4 between exons 4 and 5, leads to a modification of the reading frame during the translation of said transcript and the generation of a stop codon after aminoacid 21 of said intron 4; thus, the encoded protein does nor include neither the transmembrane region (exon 5) nor the cytoplasmic domain (exon 6) and therefore, leads to a soluble protein easy to obtain from circulating mononuclear cells, said soluble protein having very interesting immunomodulating properties.

This transcript has equally been detected in trophoblasts (J. Immunol., p. 5516–5524, 1994); however, the expression of this transcript by mononuclear cells provides, unexpectedly, a means for studying, analyzing and evaluating immunomodulation.

b) the transcript, designated HLA-G6, including intron 4, but excluding exon 3.

c) transcripts such as defined above, in a) or b), without exon 6 and/or without exon 8.

Therefore, the instant invention also relates to a procedure for obtaining immunomodulating soluble proteins, said procedure being characterised in that it comprises the construction of an expression vector in which is inserted a sequence containing intron 4, obtained from adult circulating mononuclear cells, such as the ones defined hereabove and the expression of said soluble proteins.

Expression vectors from the pBJ family may be used [B. DEVAUX et al., Generation of monoclonal antibodies against soluble human T cell receptor polypeptides, Eur. J. Immunol., 1991, 21, 2111–2119 ; V. LITWIN et al., Receptor Properties of two Varicella-Zoster Virus glycoproteins, gpI and gpIV, Homologous to Herpes Simplex Virus gE and gI, J. Virol., 1992, 66, 3643–3651 ; A. Y. LIN, Expression of T Cell Antigen receptor Heterodimers in a Lipid-Linked form, Science, 1990, 249, 677–679].

The present invention also relates to peptides, or peptide fragments, which are characterized in that they are encoded by at least one fragment as defined above, or by a fragment portion or by a combination of several fragments as defined above.

According to an advantageous embodiment of the invention, the said peptide is encoded by a fragment of HLA-G4 transcript and conforms to the following SEQ ID NO:7:

Asn—Val—Ala—Glu—Gln—Arg—Arg—Ala—Tyr—Leu—Glu—Gly—Thr—Cys—
Val—Glu—Trp—Leu—His—Arg—Tyr—Leu—Glu—Asn—Gly—Lys—Glu—Met—
Leu—Gln—Arg—Ala—Glu—Gln—Ser—Ser—Leu—Pro—Thr—Ile—Pro—Ile—
Met—Gly—Ile—Val—Ala—Gly—Leu—Val—Val—Leu—Ala—Ala—Val—Val—
Thr—Glu—Ala—Ala—Val—Ala—Ala—Val—Leu—Trp—Arg—Lys—Lys—Ser—Ser—Asp.

According to another advantageous embodiment of this invention, said peptide is encoded by a fragment of HLA-G5 and conforms to the following SEQ ID NO:8

| Asn | Val | Ala | Glu | Gln | Arg | Arg | Ala | Tyr | Leu | Glu | Gly | Thr | Cys | Val | Glu | Trp | Leu |
|---|---|---|---|---|---|---|---|---|---|---|---|---|---|---|---|---|---|
| His | Arg | Tyr | Leu | Glu | Asn | Gly | Lys | Glu | Met | Leu | Gln | Arg | Ala | Asp | Pro | Pro | Lys |
| Thr | His | Val | Thr | His | His | Pro | Val | Phe | Asp | Tyr | Glu | Ala | Thr | Leu | Arg | Cys | Trp |
| Ala | Leu | Gly | Phe | Tyr | Pro | Ala | Glu | Ile | Ile | Leu | Thr | Trp | Gln | Arg | Asp | Gly | Glu |
| Asp | Gln | Thr | Gln | Asp | Val | Glu | Leu | Val | Glu | Thr | Arg | Pro | Ala | Gly | Asp | Gly | Thr |
| Phe | Gln | Lys | Trp | Ala | Ala | Val | Val | Val | Pro | Ser | Gly | Glu | Glu | Gln | Arg | Tyr | Thr |
| Cys | His | Val | Gln | His | Glu | Gly | Leu | Pro | Glu | Pro | Leu | Met | Leu | Arg | Trp | Ser | Lys |
| Glu | Gly | Asp | Gly | Gly | Ile | Met | Ser | Val | Arg | Glu | Ser | Arg | Ser | Leu | Ser | Glu | Asp |
| Leu. | | | | | | | | | | | | | | | | | |

According to an advantageous embodiment of this invention, said peptide is encoded by a fragment of HLA-GG and conforms to the following SEQ NO: 9:

| Gln | Ser | Glu | Ala | Asn | Pro | Pro | Lys | Thr | His | Val | Thr | His | His | Pro | Val | Phe | Asp |
|---|---|---|---|---|---|---|---|---|---|---|---|---|---|---|---|---|---|
| Tyr | Glu | Ala | Thr | Leu | Arg | Cys | Trp | Ala | Leu | Gly | Phe | Tyr | Pro | Ala | Glu | Ile | Ile |

| Leu | Thr | Trp | Gln | Arg | Asp | Gly | Glu | Asp | Gln | Thr | Gln | Asp | Val | Glu | Leu | Val | Glu |
| Thr | Arg | Pro | Ala | Gly | Asp | Gly | Thr | Phe | Gln | Lys | Trp | Ala | Ala | Val | Val | Val | Pro |
| Ser | Gly | Glu | Glu | Gln | Arg | Tyr | Thr | Cys | His | Val | Gln | His | Glu | Gly | Leu | Pro | Glu |
| Pro | Leu | Met | Leu | Arg | Trp | Ser | Lys | Glu | gly | Asp | Gly | Gly | Ile | Met | Ser | Val | Arg |
| Glu | Ser | Arg | Ser | Leu | Ser | Glu | Asp | Leu. | | | | | | | | | |

According to another advantageous embodiment of the peptides according to the invention, they can be obtained by synthesis.

In conformity with the invention, peptides of this nature can be employed as medicaments, in particular in immunomodulating compositions.

The present invention also relates to a procedure for selecting, and enriching with, undifferentiated haematopoietic cells (immature blood cells or stem cells), which procedure is characterized in that it comprises:

(a) taking a sample which is selected, as the case may be, from among peripheral blood, umbilical cord blood or bone marrow, (b) bringing the said sample into contact with anti-CD34 antibodies, (DYNABEADS™ DYNAL/BIOSYS, Compiègne, France), (c) separating the cell complexes, containing a CD34 antigen-anti-CD34 antibody, which are formed, (d) carrying out an in-situ RT PCR on the cells obtained in step (c) in the presence of a pair of primers which are labelled with a fluorochrome, in accordance with the invention, (e) separating the fluorescent cells, and (f) selecting the pluripotent, immature nonfluorescent cells.

The cells obtained in (f) are CD34$^+$, HLA-G$^-$ cells, which are the most immature cells. Such a procedure advantageously makes it possible to obtain a large number of immature stem cells which are suitable for being employed for stem cell grafts.

According to an advantageous embodiment of the said procedure, the pair of primers is selected from among the pairs (1)–(2) and (3)–(4) as defined above.

The present invention also relates to a procedure for detecting cells expressing the transcript HLA-G4 according to the invention, which procedure is characterized in that it comprises the in-situ implementation of an RT PCR, by:

(a) bringing blood cells into contact with a pair of labelled primers according to the invention, selected from among the pairs (1)–(2) and (3)–(4) as defined above.

(b) separating the labelled cells by any appropriate means, in particular by cytofluorometry.

RT PCR is described, in particular, in American J. Pathol., 1993, 143, 6, 1527–1534.

The present invention also relates to a procedure for detecting blood cells and more particularly adult circulating mononuclear cells, expressing a transcript comprising intron 4, which procedure is characterized in that it comprises the in-situ implementation of a RT PCR by:

(a) bringing blood cells into contact with a pair of primers which are labelled in accordance with the invention, selected from among the pairs (1)–(2) and (3)–(4) as defined above, and (b) selecting the transcripts comprising intron 4 by hybridization with a probe, eventually labelled, selected among SEQ ID NO: 10 probe 5'-GAGGCATCATGTCTGTTAGG (designated G.i4A) and SEQ ID NO: 11 probe 5'-AAAGGAGGTGAAGGTGAGGG (designated G.i4B) and (c) separating the labelled cells by any appropriate means, in particular by cytofluorometry.

The present invention also relates to antibodies which are directed against the HLA-G proteins as defined above.

Preferably, antibodies of this nature are obtained by immunizing an appropriate animal with the peptides according to the invention.

The present invention also relates to a procedure for separating nucleated foetal cells from a sample of maternal blood, which procedure is characterized in that it comprises:

(1) bringing the sample of maternal blood into contact with antibodies which are directed against the HLA-G proteins as defined above, and (2) separating the foetal-antibody cell complexes which are obtained.

Such a procedure permits prenatal screening for foetal anomalies and, in particular, chromosomal aberrations or gene aberrations, and prenatal determination of sex, using circulating foetal cells which have thus been isolated, in a reliable manner, from the maternal blood circulation, in as much as it is only these foetal cells which carry the said HLA-G proteins.

The present invention also relates to a procedure for specifically separating circulating mononuclear cells, which procedure is characterized in that it comprises the in-situ implementation of an RT PCR by:

(a) bringing blood cells into contact with a pair of primers which are labelled in accordance with the invention, and (b) separating the labelled cells (cytofluorometry . . .).

Such a process allows, if necessary, also to separate mononuclear cells which do not express HLA-G gene (in particular natural killer cells) from other mononuclear cells.

In addition to the preceding provisions, the invention also includes other provisions, which will emerge from the description which follows, which refers to examples of implementing the procedure which is the subject matter of the present invention.

Proteins, expressed by transcripts such as defined above, have also as fonction to recognize CD8 receptors on killer T cells and therefore play a role in the immune monitoring. At the materno-foetal interface, this secreted protein could block the recognition of target structures not being part of the major histocompatibilitè complex and therefore suppress human cytotoxicity (immunologic tolerance as specified above).

The present invention also relates to a method of detection of CD8 receptors, which procedure is characterized in that it comprises bringing mononuclear cells into contact with a peptide as defined hereabove and detecting CD8-peptide complexes by any appropriate means (in particular formation of an antigen-antibody complex).

Moreover, only NK cells (or natural killer cells) do not express HLA-G MARN; this clearly shows that expression products of HLA-G gene protect against lytic activity of NK cells.

It should be understood, however, that these examples are solely provided for the purpose of illustrating the subject matter of the invention, to which they in no way constitute a limitation.

EXAMPLE 1

Transcript of the spliced HLA-G gene, without exon 4 a) Obtaining adult cells and foetal tissues

Trophoblasts from the first trimester of gestation are obtained at voluntary termination of pregnancy (6–10 weeks of gestation).

Foetal livers from the second trimester are obtained at therapeutic terminations of pregnancy (16 weeks of gestation).

The tissues are washed in a PBS buffer and the trophoblasts or the liver are identified under a microscope and frozen in liquid nitrogen.

Samples of peripheral human blood are obtained from volunteers (healthy persons).

Mononuclear cells are separated from polynuclear cells by density centrifugation (FICOLL-HYPAQUE®) and the mRNA is isolated from the two populations.

Mononuclear cells which are enriched in B mononuclear cells are also obtained by immunoabsorption onto magnetic beads which are coated with anti-CD19 antibodies (DYNABEADS™-Dynal/Biosys, France), and mononuclear cells enriched in T mononuclear cells are obtained by separation on Leuko-Pac™ (Fenwal Laboratories, USA).

The enrichment is approximately 90% for the B cells and approximately 87% for the T cells, as estimated by FACS analysis: an assessment of the complexes which are formed with anti-CD20 antibodies or anti-CD3 antibodies, respectively, with the antibodies being labelled with FITC, and with $1.10^5$ cells being taken from each subpopulation.

b) Isolation of the RNA and amplification by means of RT PCR

The total mRNA is isolated from 1 g of frozen tissue or from $2.10^7$ cells using the reagent RNA-Zol B (Bioprobe Systems, France) in accordance with the manufacturer's recommendations; the quality of the product obtained is checked by electrophoresis on a denaturing 1.5% agarose gel.

The cDNA is prepared from 10 μg of total RNA, in the presence of oligo-dT primer and M-MLV reverse transcriptase (Gibco-BRL, Life Technologies), by incubating 20 μl of the mixture at 42° C. for 1 hour and then at 95° C. for 5 minutes.

The PCR fragments which can be obtained with the primers which are employed (see Table I below) are depicted in FIG. 1.

The primers G.526 and G.1225 (represented by horizontal arrows) are preferably used in order to amplify the G.3-5 transcript (now designated HLA-G4) according to the invention (fragment of 0.43 kb); the G.3-5 probe (represented by a thick line) is employed for detecting this amplified transcript.

The vertical arrows indicate the specific restriction sites in exons 3, 4 and 5 which are used for the restriction analysis of the RT PCR products, which are cloned into the vector pPCRII (B: BglI; St: StuI; Ss: SstI).

TABLE I

| Primer | 5' → 3' sequence | Location cDNA | genomic DNA |
|---|---|---|---|
| G.257 (+) (SEQ ID NO:2) | GGA AGA GGA GAC ACCG GAA CA | 257–276 | Ex 2 |
| G.526 (+) (SEQ ID NO: 3) | CCA ATG TGG CTG AAC AAA GG | 526–545 | Ex 3 |
| G.1200 (−) (SEQ ID NO: 4) | CCC CTT TTC TGG AAC AGG AA | 1200–1219 | 3'-UT |
| G.1225 (−) (SEQ ID NO: 5) | TGA GAC AGA GAC GGA GAC AT | 1225–1244 | 3'-UT |
| G.3-5 (+) (SEQ ID NO: 6) | CAG CGC GCG GAG CAG TCT TC | 615–624/ 901–910 | Ex 3/ Ex 5 |
| Class I (+) | TCC CAC TCC ATG AGG TAT TTC | 81–100 | Ex 2 |
| Class I (−) | TCC AGA AGG CAC CAC CAC AG | 814–833 | Ex 4 |

In order to reduce the quantity of non-specific amplified product, the amplification is carried out using a technique which is termed "hot-start": 200 μM of each dNTP, 0.1 μg of each primer and a chip of AMPLIWAX® wax beads (Cetus-Perkin Elmer, France) are incubated, at 75° C. for 5 min, in 50 μl of a 1×PCR buffer in a first reaction tube; 2 μl of the RT solution or 1 μg of genomic DNA and 3.5 U of Taq polymerase (Cetus-Perkin Elmer) are incubated, at 95° for 5 min, in 50 μl of the 1×PCR buffer in a second tube.

The contents of the 2 tubes are then mixed and submitted to 35 PCR cycles under the following conditions:

94° C. for 1 minute,

61° C. for 1 minute, and

72° C. for 1 minute 30 seconds.

The final elongation step at 72 C. lasts for 10 min.

The PCR products are analysed by electrophoresis in a 1% agarose gel, and stained using ethidium bromide.

The specificity of the products obtained is confirmed by blotting the fragments, under alkaline conditions (0.4N NaOH), onto a nylon membrane (Hybond N⁺, Amersham, France), with a hybridization then being carried out in the following buffer: 5×SSPE, 5×Denhardt's, 0.5% SDS and 100 μg/ml salmon sperm DNA; the incubation is carried out at 55° C. for 2 h in the presence of a G-1200 oligonucleotide probe which is labelled with $^{32}$P ([γ-$^{32}$P]dATP) and a kit for labelling the 5' end (Boehringer-Mannheim, France).

Various amplification controls are carried out: RT reaction mixture without M-MLV reverse transcriptase (RT), and PCR mixture without cDNA template (blank).

Furthermore, positive controls are carried out using universal primers for HLA class I (see Table I).

c) Results

Figure 2A:
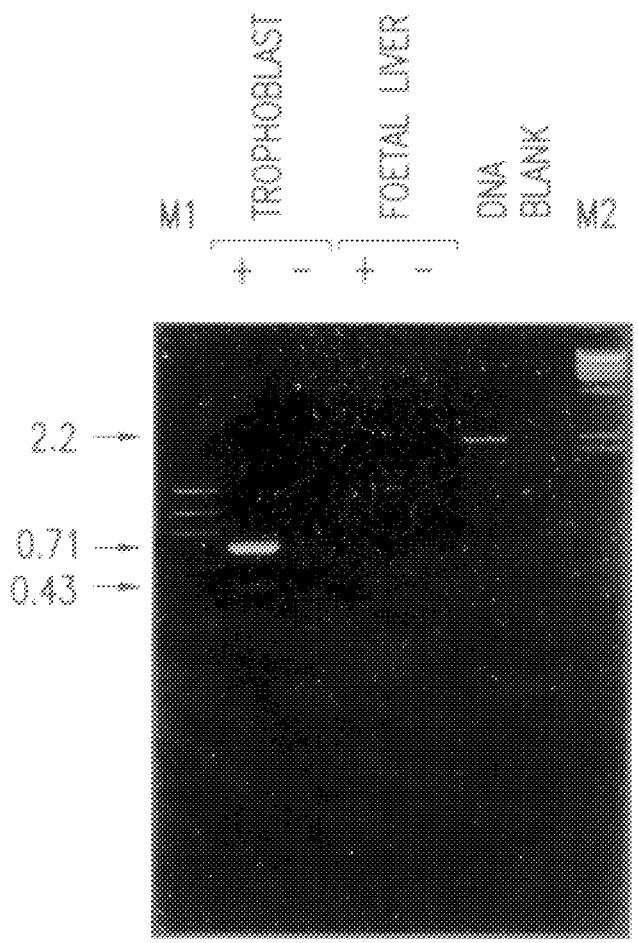
Figure 2B:
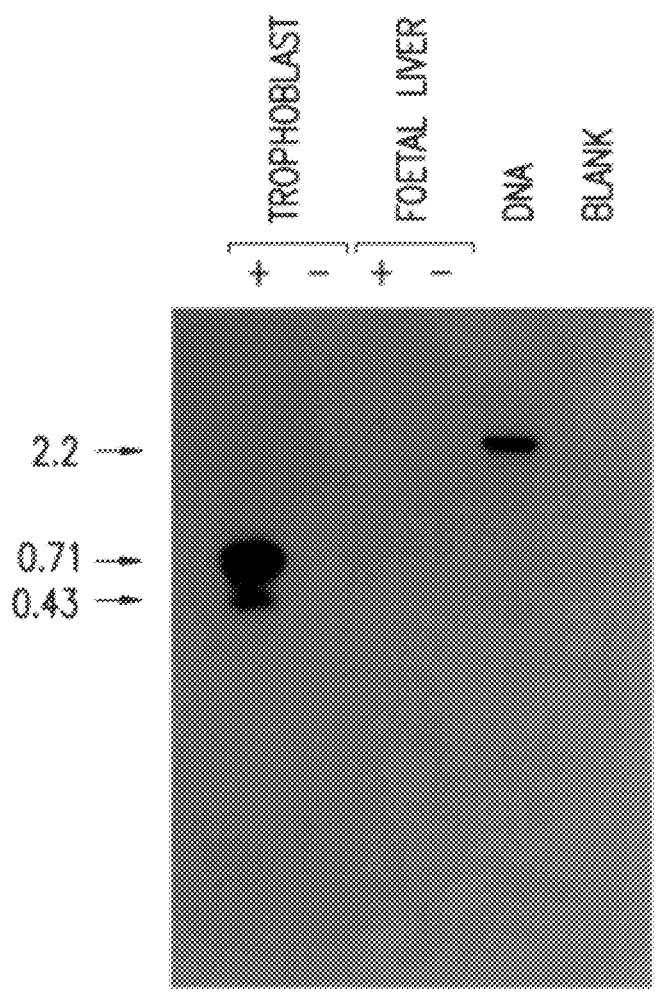

1. Using the primers G.526 and G.1225, two fragments (0.71 kb and 0.43 kb) are observed, following gel electrophoresis and ethidium bromide staining, which hybridize to the G1200 probe (see FIG. 1 and FIGS. 2a and 2b).

Figure 2C:
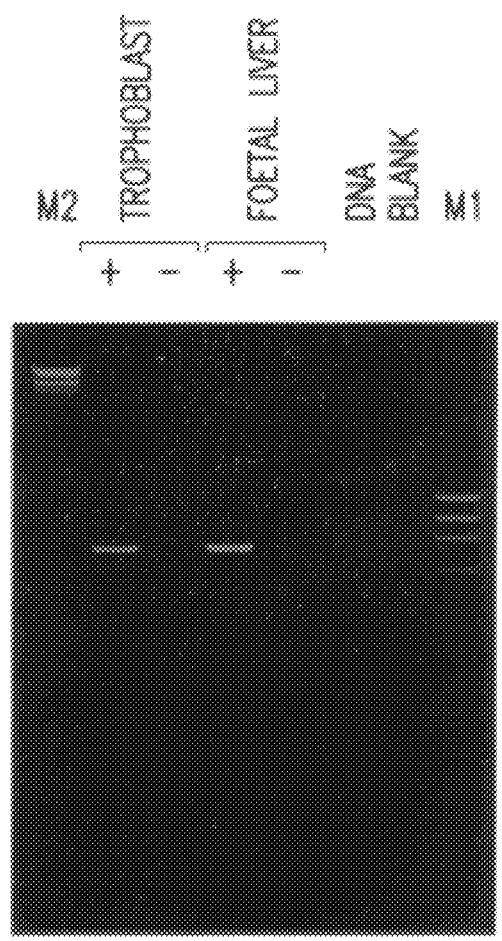

2. The RT PCR on the mRNA from the foetal liver of the 2nd trimester does not yield any band on the gel, nor any hybridization signal, whereas amplification using HLA class I primers results in a positive signal (FIG. 2C).

Amplification of the genomic DNA yields a band at approximately 2.2 kb, in conformity with the HLA-G genomic sequence.

3. The 0.71 kb fragment corresponds to the complete HLA-G transcript while

4. The 0.43 kb fragment corresponds to a transcript which does not contain exon 4 (–>276 bp) (HLA-G4).

In order to confirm the absence of exon 4, the band of 0.43 kb is cut out and sequenced according to the following method:

In order to generate sequencing templates, the PCR fragments are separated by electrophoresis on a 4% polyacrylamide gel, cut out and eluted using an 0.5M ammonium acetate, 5 mM EDTA buffer, and then reamplified by asymmetrical PCR in order to generate single-strand products.

The reamplified product is purified by extracting it with phenol/chloroform, and precipitating it twice with ethanol; it is then sequenced using the T7 Sequenase 2.0 sequencing kit (USB/Touzard-Matignon, France).

In addition, the products of the PCR are cloned into vector pPCRII using the TA Cloning System kit (Invitrogen, USA), and then sequenced.

Figure 3A:
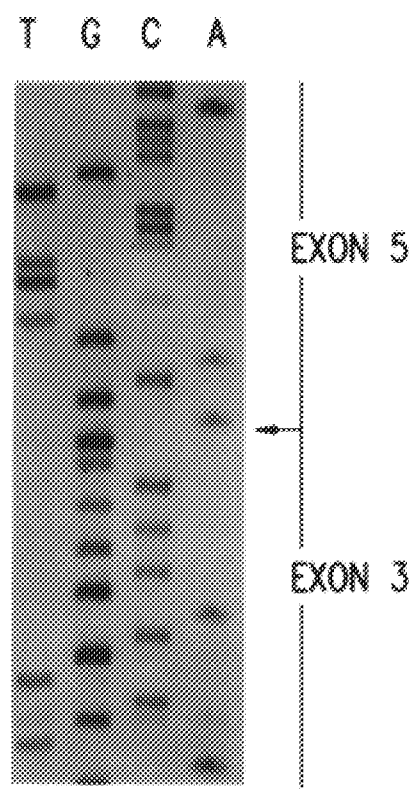
Figure 3B:
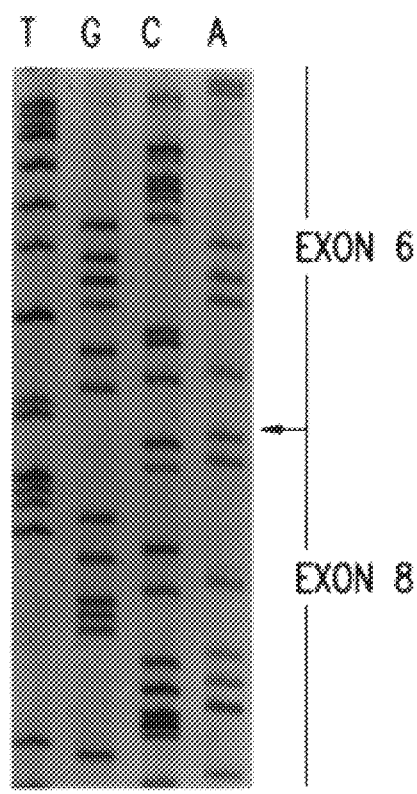

As FIG. 3 shows, the 0.43 kb fragment clearly displays a junction between exon 3 and exon 5, resulting from the loss of exon 4.

In addition, the sequencing demonstrates that the transcript according to the invention does not encompass exon 7; furthermore, the presence is observed of a stop codon in exon 6.

5. Assessment of the frequency of the HLA-G4 as suggested by FIG. 2, the hybridization intensity of the band of 0.43 kb, corresponding to the spliced transcript, is weaker than that corresponding to the complete copy; this suggests that this transcript is less abundant in the HLA-G mRNA population.

In order to assess the relative quantities of these two transcripts, the products from PCR amplification of the mRNA from trophoblasts of the first trimester using the primers G.526 and G.1225 are cloned into vector pPCRII as explained above.

Out of 260 clones which are analysed by replica hybridization, on the one hand using probe G1200 and on the other using probe G.3-5, approximately 210 clones display a positive hybridization with probe G.1200, and only one clone is positive with the G.3-5 probe.

This single clone was sequenced while 5 clones which were positive with the G.1200 probe, and which were selected at random, were analysed on the basis of their restriction map which was determined using enzymes which were specific for exons 3 and 4 (see FIG. 1).

A comparison of the sequences demonstrates that the clone which hybridizes and is positive with probe G.3-5 does not contain exon 4, whereas the other 5 clones correspond to the complete transcript.

Thus, the frequency of the transcript according to the invention, as compared with that of the transcript containing the complete sequence, can be estimated to be approximately 1/200.

Choosing primer G.526 (specific for exon 3) for the PCR amplification enabled a transcript lacking exon 4 to [be] selected.

The absence of exon 4 creates a GAG (Glu) codon at the splicing junction in place of the GAC (Asp) codon which is found in the complete transcript.

The absence of exon 4 excludes the α3 domain from the corresponding, deduced protein, and confers a novel structure on the HLA-G antigen which can be expressed on the surface of the trophoblast cells.

In this structure, the α2 domain and the transmembrane region are linked together and are able to induce confirmational modifications in the surface protein.

In particular, the said protein can exhibit an altered capacity for binding to peptides.

EXAMPLE 2

Figure 4A:
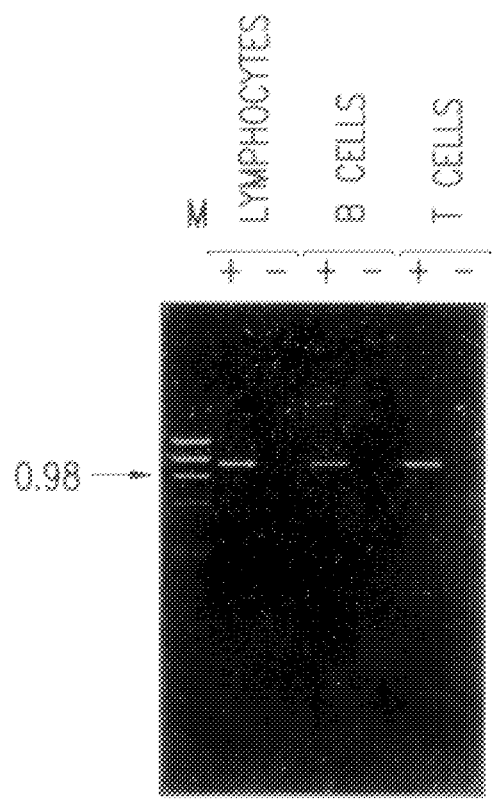

Expression of the complete HLA-G transcript, or of the transcript without exon 4, in adult circulating peripheral mononuclear cells FIG. 4 shows the PCR amplification results which were obtained with the primers G.257 and G.1225 using cDNA templates from peripheral mononuclear cells which were obtained from human patients (male subjects).

Figure 4B:
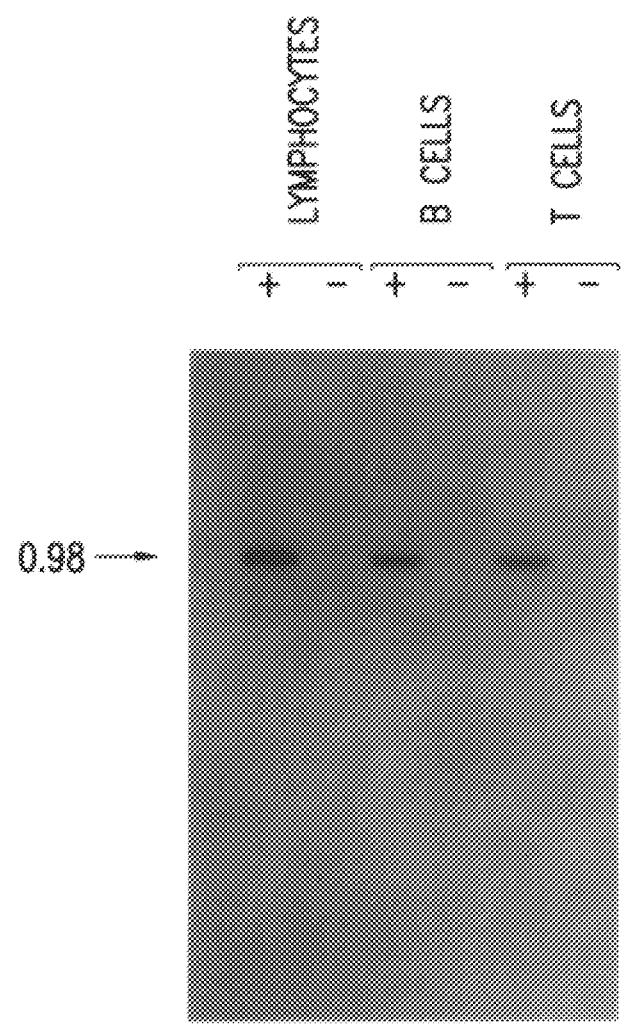

A band of 1 kb is observed in an agarose gel (FIG. 4a); hybridization with probe G.1200 reveals a band of the same size (FIG. 4b).

In conformity with the cDNA sequence, this band corresponds to the complete HLA-G transcript.

In order to confirm production of this transcript, the PCR product is cloned into a pPCRII vector and then sequenced by the method described above.

The 1 kb fragment is entirely homologous with the HLA-G sequence described by SHUKLA et al. (Nucleic Acids Research, 1990, 18, 8, 2189).

PCR amplification of the cDNA from a population of polynuclear cells using HLA-G specific primers generates a band of weak intensity of the same size, 0.71 kb, as that observed with the mononuclear cells (contamination of the polynuclear cell fraction with mononuclear cells).

In order to clarify the cellular specificity of the expression of the HLA-G gene in adult circulating mononuclear cells, the mononuclear cell populations were separated, and a PCR was carried out, using HLA-G specific primers, on the cDNA obtained from subpopulations enriched either in T cells or in B cells.

For the T cell fractions, a 1 kb band is observed both in an agarose gel and in a blot analysis following hybridization to probe G.1200 (FIGS. 4A and B) (complete transcript).

The use of a hot-start PCR technique enabled the presence of HLA-G mRNA to be demonstrated in adult peripheral mononuclear cells, with this transcript being present at one and the same time in the B cells and in the T cells.

All the alternative transcripts are observed in peripheral blood mononuclear cells.

EXAMPLE 3

Transcript of HLA-G gene comprising intron 4 a) Isolation of adult cells and fetal tissues

It is proceeded as example 1.

b) RNA isolation, extraction and amplification by PCR

Total RNA from 1 g of trophoblasts or $2 \times 10^7$ mononuclear cells was prepared using RNA Zol B reagent (Bioproble System, Paris) according to the manufacturer's recommendations.

For extraction of cytoplasmic RNA, cells were lysed 5 min in a ice-cold buffer containing 50 mM Tris/HCl, pH 8.0, 100 mM NaCl, 5 mM $MgCl_2$, 0,5% NONIDET™ P-40 detergent and 10 mM ribonucleoside vanadyl complexes (Sigma Chemical, St Louis). The intact nuclei were removed by centrifugation 2 min at 12.000 g and the supernatant proteins were denatured with 4 µl of 20% SDS, then digested with 2,5 µl of 20 mg/ml proteinase K for 15 min at 37° C.

After phenol/chloroform and chloroform extractions, cytoplasmic RNA was recovered by ethanol precipitation in presence of 3M sodium acetate. The quality of RNA was examined by electrophoresis in 1.5% agarose gel in presence of formaldehyde.

cDNA is prepared from 5 to 10 µg of total RNA with oligo-dT priming and M-MLV reverse transcriptase (Gibco- BRL, Life Technologies, Grand Island, N.Y.) according to Example 1 procedure.

PCR amplifications (DNA thermal cycler, Cetus/Perkin-Elmer) were performed with hot-start technique conditions as described previously, using the HLA-G primers G.526 (exon 3 specific) and G.1225 (3' untranslated region) for 35 cycles at the following conditions: 94° C. for 1 min, 61° C. for 1 min 30 sec and 72° C. for 2 min.

Absence of contaminant DNA was controlled by concomitant amplification of PCR mixture without M-MLV RT (RT-) and without template (blank). Specificity of RT PCR products was examined as previously described in Example 1, by Southern blot with $^{32}$P 5'-end labelled oligonucleotide G.1200 probe. For the detection of intron 4, we used the oligonucleotide probe G.i4A (5'-GAGGCATCATGTCTGTTAGG) of SEQ ID NO:10 or the probe G.i4B (5'-AAAGGAGGTGAAGGTGAGGG) of SEQ ID NO: 11.

After two washes of 15 min at room temperature and two washes of 15 min at 50° C. in presence of 2×SSC, 0.1% SDS the blots were exposed to Fuji X-RAY film with intensifying screens at −80° C.

c) Isolation and sequencing of RT PCR products

The RT PCR products were cloned in PCR II vector sing a TA cloning system kit (Invitrogen, San Diego, Calif.) as recommended by the manufacturer. Transformation was performed with Max efficiency DHα5FIQ competent cells (Gibco-BRL, Life Technologies, Grand Island, N.Y.) and screening of HLA-G recombinant clones was carried out by hybridization of replicas with G.1200 probe. The inserts were excised by EcoRI digestion and discriminated according to their molecular weight on 1% agarose gel. Evaluation of frequency of transcript containing intron 4 was deduced from the number of colonies in replicas showing positive hybridization with intron 4 probe (G.i4) versus number of clones showing positive hybridization with G.1200 probe. For the detection of exons 4 and 5, the oligonucleotide probes G.647 (5'-CCACCACCCTGTCTTTGACT (SEQ ID NO:13)) and G.927 (5'-ATCATGGGTATCGTTGCTGG (SEQ ID NO:14)) were respectively used. Absence of DNA insertion was controlled by the oligonucleotide probe G.7 (5'-CTAATGTGTCTCTCACGGCT (SEQ ID NO:15)), specific of exon 7. Clones of interest were subjected to asymmetric PCR to generate single-strand templates and subsequently sequenced by using a T7 Sequenase 2.0 sequencing kit (U.S.B., Touzard-Matignon, France), as illustrated hereabove.

d) Results

Figure 5:
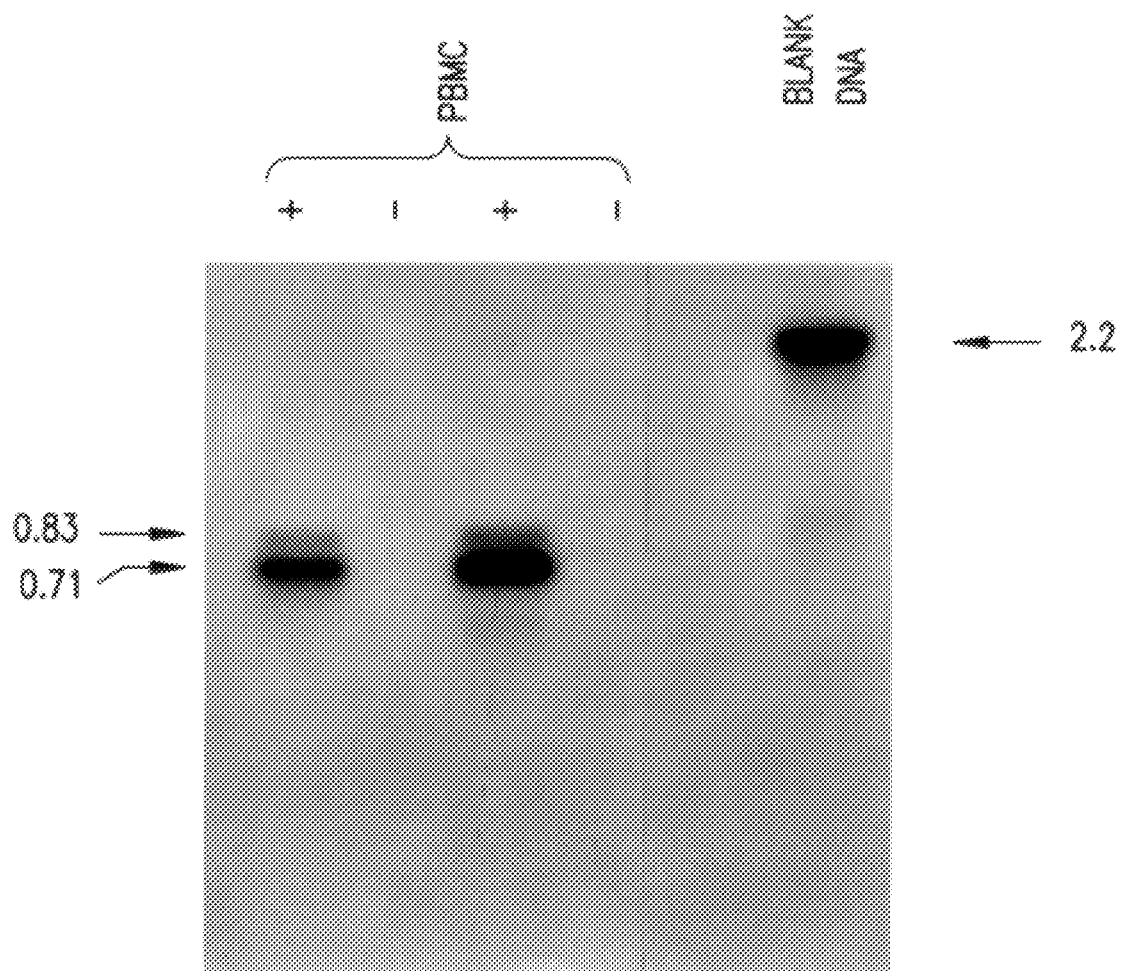

1) Identification of an alternatively spliced HLA-G transcript interrupted by intron 4 in mononuclear cells from adult human peripheral blood and first trimester trophoblasts Gel electrophoresis of G.526-G.1225 primed RT PCR products obtained from total RNA of male adult peripheral blood mononuclear cells and hybridization with G.1200 probe reveals a band at 0.83 kb in addition to the major band corresponding to HLA-G1 mRNA (0.71 kb) (FIG. 5). This fragment is still detected after hybridization of RT PCR products from cytoplasmic RNA.

Figure 6A:
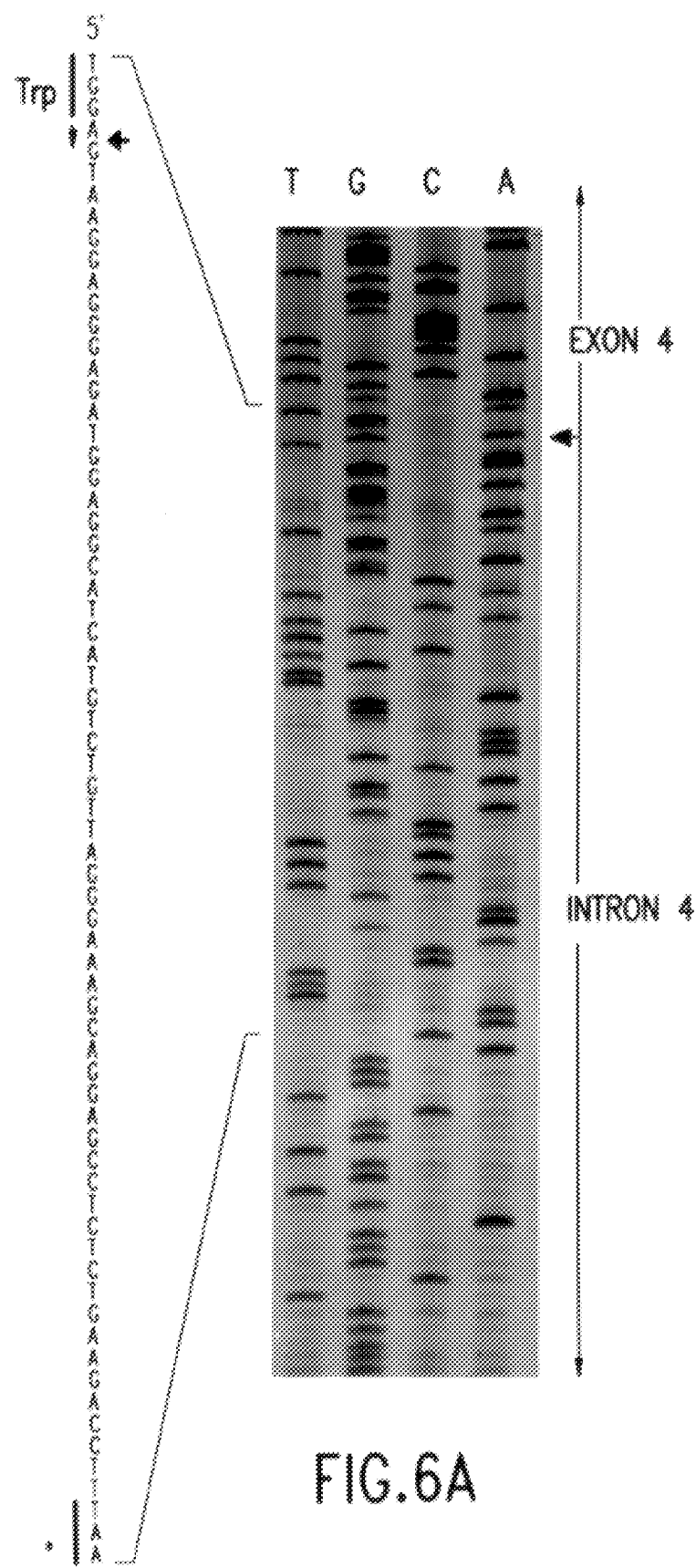
Figure 6B:
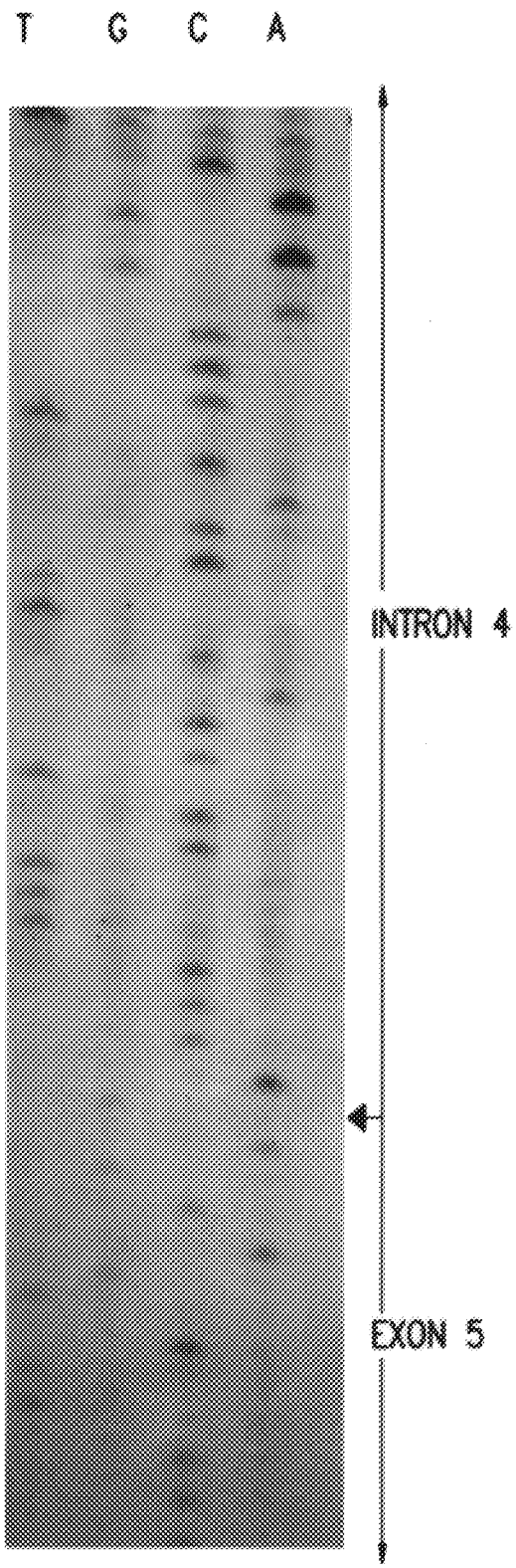

In order to characterize the nature of that large fragment, total RT PCR product from peripheral blood mononuclear cells was cloned in pPCRII vector, as specified hereabove. G.1200 positive clones were analysed by EcoRI digestion, selected for the insert length and sequenced. The sequence demonstrates that the 0.83 kb fragment presents an additional segment of 122 bp between exon 4 (FIG. 6A) and exon 5 (FIG. 6B).

Comparison with genomic HLA-G sequence indicates that this fragment corresponds to the intron 4.

Figure 6C:
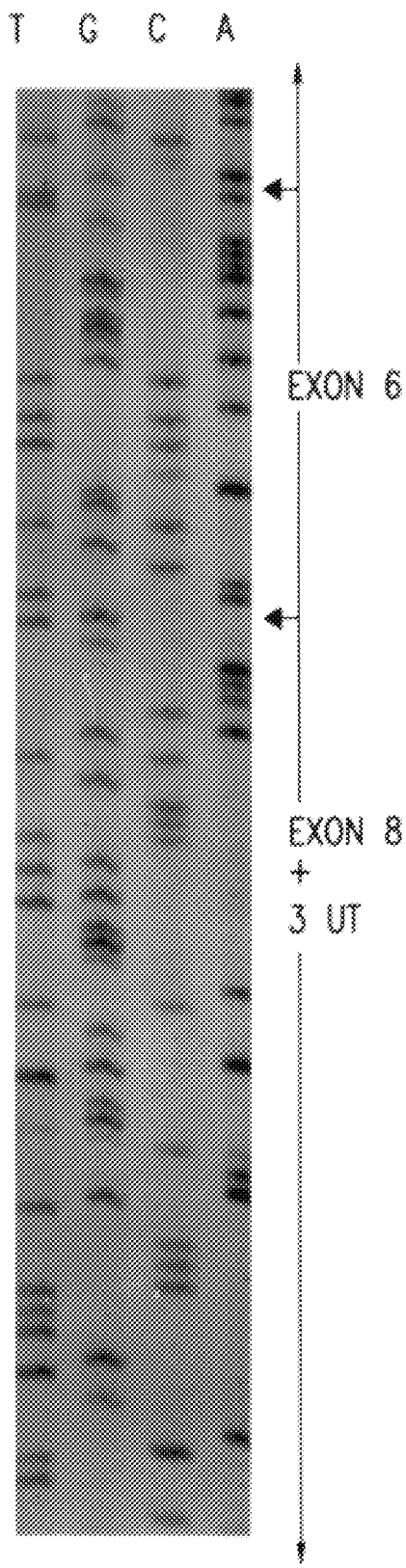

Moreover, sequencing of the 3' adjacent region reveals the absence of exon 7 (FIG. 6C) as previously observed for all other alternatively spliced forms of HLA-G mRNA.

Figure 6D:
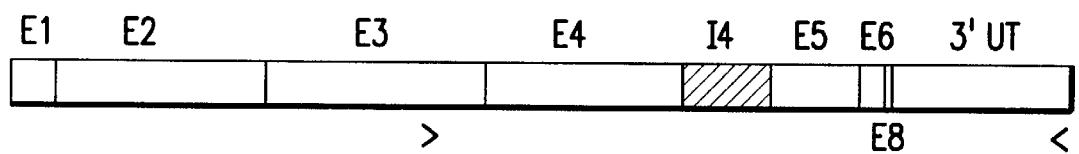

This new alternative form is hereafter designated HLA-G5 according to the nomenclature of HLA-G transcripts (FIG. 6D).

Search for HLA-G5 in first trimester trophoblasts was carried out by Southern blot hybridization of the PCR products generated by G.526-G.1225 primers using the intron 4 specific oligonucleotide probe G.i4A.

Figure 7:
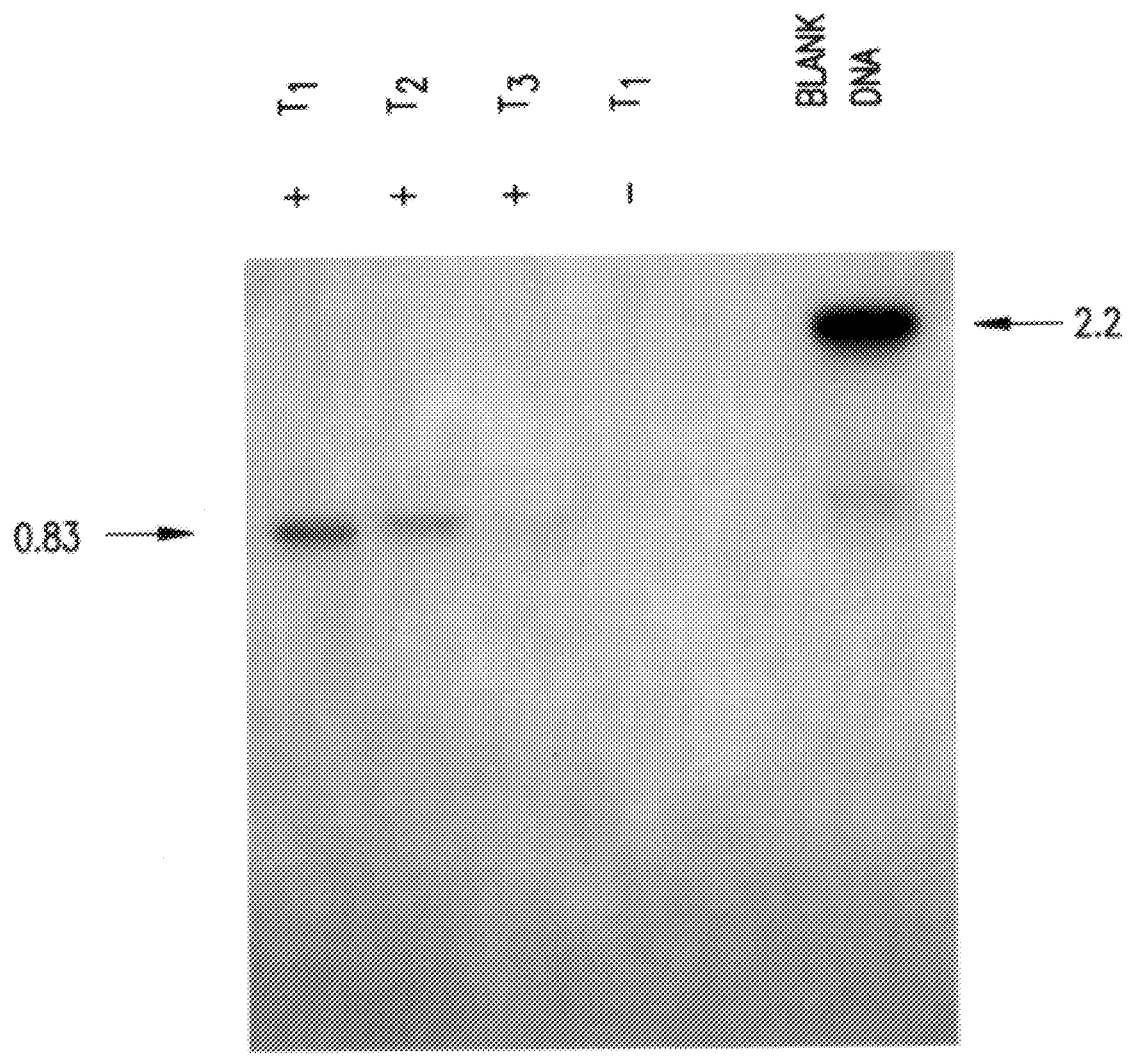

FIG. 7 shows presence of one band at 2.2 kb (genomic DNA) and one band at approximately 0.83 kb in all the tissues examined (HLA-G5 fragment length).

To confirm this result, the trophoblast PCR product have been screened with the G.i4A probe after cloning in pPCRII vector.

Sequencing of two positive clones has demonstrated the same organization as in peripheral blood mononuclear cells.

HLA-G6 transcript has also been detected by specific amplification of a G-3 probe (junction exon 2-exon 4: 5'ACCAGAGCGAGGCCAACCCC) (SEQ ID NO: 12) and G.i4B probe (SEQ ID NO: 11).

2) Estimation of frequency of HLA-G transcripts containing intron 4

A first hybridization has been performed with G.i4A probe and secondly G.1200 probe on replicas obtained after cloning of total RT PCR product from first trimester trophoblasts and adult peripheral blood mononuclear cells generated by G.526-G.1225 primer sets. Absence of genomic DNA insertions was controlled after hybridization of replicas with the exon 7 specific probe (G.7) and presence of exon 4 and 5 was demonstrated by hybridization with the probes G.647 and G.927. Of 437 clones from peripheral blood mononuclear cells showing a positive hybridization with G.1200, 55 clones were positive with G.i4A probe: of 210 clones from first trimester trophoblasts showing a positive hybridization with G.1200, 8 clones gave a positive hybridization with G.i4A probe. The results show that frequency of HLA-G mRNA interrupted by intron 4 is higher in peripheral blood mononuclear cells than in trophoblasts: the ratio G.i4/G.1200 positive clones is 1:8 for peripheral blood mononuclear cells and 1:26 for trophoblasts.

It emerges from these results that an HLA-G mRNA interrupted by intron 4 between exons 4 and 5 was present in vivo both in adult peripheral blood mononuclear cells and first trimester human trophoblasts with highest abundance in the case of hematopoietic material.

As regards the HLA-G protein, obtained with such a transcript, it is important to note that intron 4 sequence introduces a stop codon at nucleotide 63 downstream from the 3' end of exon 4.

Early stop codon upstream of exon 5 was also observed.

Unexpectedly such a transcript not including exon 5 (region encoding transmembrane protein) permits the obtention of soluble proteins which are particularly useful as immunomodulating product.

As can be seen from that which has been written above, the invention is in no way limited to those of its modes of implementation, of realization and of application which have been described more explicitly; on the contrary, it encompasses all the variants which may be conceived by the person skilled in the art without departing from the scope, or the import, of the present invention.

We claim:

1. A protein encoded by a transcript of the human MHC HLA-G gene, wherein said transcript comprises in succession from the 5' end to the 3' end:

a sequence encoding the α2 domain;

a sequence encoding the transmembrane domain; and a sequence encoding the cytoplasmic domain;

said transcript not containing a sequence encoding the α3 domain.

2. The protein of claim 1, wherein said transcript additionally comprises:

a sequence encoding the signal peptide located on the 5' side of said sequence encoding the α2 domain;

a sequence encoding the α1 domain located between said sequence encoding the signal peptide and said sequence encoding the α2 domain; and a sequence encoding the 3' untranslated region located on the 3' side of said sequence encoding the cytoplasmic domain.

3. A polypeptide which has the amino acid sequence of SEQ ID NO:7.

4. The protein of claim 1, wherein said transcript additionally comprises:

a sequence encoding the 3' untranslated region located on the 3' side of said sequence encoding the cytoplasmic domain.

5. The protein of claim 4, wherein said transcript has the nucleotide sequence of SEQ ID NO:1.

6. The protein of claim 1, wherein said transcript additionally comprises:

a sequence encoding the signal peptide located on the 5' side of said sequence encoding the α2 domain; and a sequence encoding the α1 domain located between said sequence encoding the signal peptide and said sequence encoding the transmembrane domain.

7. A protein encoded by a transcript of the human MHC HLA-G gene, wherein said transcript comprises in succession from the 5' end to the 3' end:

a sequence encoding the signal peptide;

a sequence encoding the α1 domain;

a sequence encoding the α3 domain;

intron 4; and a sequence encoding the transmembrane domain.

8. The protein of claim 7, wherein said transcript additionally comprises:

a sequence encoding the α2 domain located between said sequence encoding the α1 domain and said a sequence encoding the α3 domain;

a sequence encoding the cytoplasmic domain located on the 3' side of said sequence encoding the transmembrane domain; and a sequence encoding the 3' untranslated region located on the 3' side of said sequence encoding the cytoplasmic domain.

9. A polypeptide having the amino acid sequence of SEQ ID NO:8.

10. The protein of claim 7, wherein said transcript additionally comprises:

a sequence encoding the cytoplasmic domain located on the 3' side of said sequence encoding the transmembrane domain; and a sequence encoding the 3' untranslated region located on the 3' side of said sequence encoding the cytoplasmic domain.

11. A polypeptide which has the amino acid sequence of SEQ ID NO:9.

12. The protein of claim 7, wherein said transcript additionally comprises:

a sequence encoding the α2 domain located between said sequence encoding the α1 domain and said a sequence encoding the α3 domain; and a sequence encoding the 3' untranslated region located on the 3' side of said sequence encoding transmembrane domain.

13. The peptide of claim 7, wherein said transcript additionally comprises:

a sequence encoding the α2 domain located between said sequence encoding the α1 domain and said a sequence encoding the α3 domain.

14. A composition, comprising the protein of claim 1 and a carrier.

15. A composition, comprising the protein of claim 7 and a carrier.

16. A method for producing an antibody, comprising the step of immunizing an animal with the protein of claim 1 and recovering said antibody.

17. A method for producing an antibody, comprising the step of immunizing an animal with the protein of claim 7 and recovering said antibody.

18. A method for detecting CD8 receptors, comprising the steps of:

(a) contacting a sample containing CD8 receptors with the protein of claim 1; and (b) detecting the CD8-protein complex.

19. A method for detecting CD8 receptors, comprising the steps of:

(a) contacting a sample containing CD8 receptors with the protein of claim 7; and (b) detecting the CD8-protein complex.

20. A water soluble protein encoded by a transcript of a human MHC HLA-G gene, wherein said transcript comprises in succession from the 5' end to the 3' end:

a sequence encoding the signal peptide;

a sequence encoding the α1 domain;

a sequence encoding the α3 domain, and intron 4, said transcript not including a sequence encoding the transmembrane domain.

21. A protein encoded by a transcript of the human MHC HLA-G gene, wherein said transcript comprises in succession from the 5' end to the 3' end:

a sequence encoding the signal peptide;

a sequence encoding the α1 domain;

a sequence encoding the α2 domain;

intron 4;

a sequence encoding the transmembrane domain;

a sequence encoding the cytoplasmic domain located on the 3' side of said sequence encoding the transmembrane domain.

* * * * *

UNITED STATES PATENT AND TRADEMARK OFFICE
CERTIFICATE OF CORRECTION

PATENT NO. : 5,856,442
DATED : January 5, 1999
INVENTOR(S) : Edgardo D. Carosella, et al.

It is certified that error appears in the above-identified patent and that said Letters Patent is hereby corrected as shown below:

Column 23, Line 19, delete "transmembrane" insert --$\alpha 2$--.

Column 24, Line 7, delete "peptide" insert --protein--.

Signed and Sealed this

Fifteenth Day of June, 1999

Attest:

Q. TODD DICKINSON

*Attesting Officer*   *Acting Commissioner of Patents and Trademarks*